US008426629B2

(12) United States Patent
Tanaka et al.

(10) Patent No.: US 8,426,629 B2
(45) Date of Patent: Apr. 23, 2013

(54) PROCESS FOR PRODUCTION OF PHOSPHINE DERIVATIVE FROM PHOSPHINE OXIDE DERIVATIVE

(75) Inventors: Hideo Tanaka, Okayama (JP); Manabu Kuroboshi, Okayama (JP); Tomotake Yano, Okayama (JP); Masakatsu Hoshino, Okayama (JP); Hiromu Kawakubo, Tokyo (JP)

(73) Assignees: National University Corporation Okayama University, Okayama (JP); Asahi Kasei Chemicals Corporation, Tokyo (JP); Hokko Chemical Industry Co., Ltd., Tokyo (JP)

( * ) Notice: Subject to any disclaimer, the term of this patent is extended or adjusted under 35 U.S.C. 154(b) by 136 days.

(21) Appl. No.: 12/991,931

(22) PCT Filed: May 14, 2009

(86) PCT No.: PCT/JP2009/058980
§ 371 (c)(1),
(2), (4) Date: Nov. 10, 2010

(87) PCT Pub. No.: WO2009/139436
PCT Pub. Date: Nov. 19, 2009

(65) Prior Publication Data
US 2011/0065961 A1    Mar. 17, 2011

(30) Foreign Application Priority Data

May 15, 2008  (JP) .............................. 2008-128632
Nov. 7, 2008  (JP) .............................. 2008-286916
Dec. 25, 2008 (JP) .............................. 2008-329498

(51) Int. Cl.
*C07F 9/28* (2006.01)

(52) U.S. Cl.
USPC ............ 558/113; 558/275; 558/189; 558/122

(58) Field of Classification Search .................... 568/17; 536/124; 558/275, 189, 122, 113
See application file for complete search history.

(56) References Cited

U.S. PATENT DOCUMENTS

| | | | |
|---|---|---|---|
| 3,405,180 A | 10/1968 | Natoli | |
| 3,481,988 A | 12/1969 | Wunsch et al. | |
| 3,780,111 A | 12/1973 | Young et al. | |
| 4,036,889 A | 7/1977 | Chopdekar | |
| 4,246,204 A | 1/1981 | Broger | |
| 4,249,023 A | 2/1981 | Broger | |
| 4,301,301 A | 11/1981 | Fukui et al. | |
| 4,727,193 A | 2/1988 | Dockner | |
| 4,758,315 A * | 7/1988 | Folest et al. ................... 205/420 |
| 5,527,966 A * | 6/1996 | Hermeling et al. .............. 568/16 |
| 5,527,967 A * | 6/1996 | Millauer .......................... 568/17 |
| 5,648,549 A * | 7/1997 | Kleiner ............................ 568/17 |
| 5,689,005 A | 11/1997 | Hagemeyer et al. | |
| 5,792,884 A | 8/1998 | Wettling | |
| 6,084,133 A * | 7/2000 | Kawashima ....................... 568/8 |

FOREIGN PATENT DOCUMENTS

| | | |
|---|---|---|
| DE | 1 247 310 | 8/1967 |
| DE | 26 38 720 A1 | 3/1977 |
| DE | 195 32 310 A1 | 3/1997 |
| EP | 0 548 682 A1 | 6/1993 |
| EP | 0 761 676 A2 | 3/1997 |
| IN | 225752 | 12/2008 |
| JP | 53-34725 A | 3/1978 |
| JP | 55-149293 A | 11/1980 |
| JP | 55-149294 A | 11/1980 |
| JP | 62-4294 A | 1/1987 |
| JP | 62-56879 B | 11/1987 |
| JP | 63-26115 B | 5/1988 |
| JP | 63-137188 A | 6/1988 |
| JP | 7-76592 A | 3/1995 |
| JP | 8-48692 A | 2/1996 |
| JP | 8-225468 A | 9/1996 |
| WO | 2005/031040 A2 | 4/2005 |

OTHER PUBLICATIONS

Dessy R.E. et al, 1966; Journal of the American Chemical Society, 88, 3, 467-470.*
English language Abstract for EP 0268526 A2, corresponding to JP 63-137188A published Jun. 9, 1988.
English language Abstract for EP 0684248 A1, corresponding to JP 8-48692A published Feb. 20, 1996.
English language Abstract for EP 0207432 A1, corresponding to JP 62-4294A published Jan. 10, 1987.
English language Abstract for EP 0716061 A1, corresponding to JP 8-225468A published Sep. 3, 1996.
Coumbe et al., "Titanium (IV) Catalysis in the Reduction of Phosphine Oxides" *Tetrahedron Letters* vol. 35, No. 4, pp. 625-628, 1994.
Fritzsche et al., "Reduktion tertiarer Phosphinoxyde zu tertiaren Phosphinen mit Trichlorsilan", *Chem. Ber.* 97, pp. 171-174, 1965.
Handa et al., "Rapid and Mild Deoxygenation of Organoheteroatom Oxides with the Efficient Electron Transfer System $SmI_2$-Tetrahydrofuran-Hexamethylphosphorric Triamide" *J. Chem. Soc., Chem. Commun.*, pp. 298-299, 1989.
Horner et al., "Wege zur Darstellung primarer, sekundarer and tertiarer Phosphine" *Chem. Ber.* 91, pp. 1583-1588, 1958.
Imamoto et al., "Stereospecific Reduction of Phosphine Oxides to Phosphines by the Use of a Methylation Reagent and Lithium Aluminum Hydride" *Organic Letters*, vol. 3, No. 1, pp. 87-90, 2001.
Imamoto et al., "Facile Reduction of Organic Halides and Phosphine Oxides with $LiAlH_4$-$CeCl_3$" *Chemistry Letters*, The Chemical Society of Japan, pp. 1491-1492, 1985.

(Continued)

*Primary Examiner* — Johann Richter
*Assistant Examiner* — Pancham Bakshi
(74) *Attorney, Agent, or Firm* — Greenblum & Bernstein, P.L.C.

(57) ABSTRACT

Disclosed is a process for producing a phosphine derivative from a phosphine oxide derivative, which comprises the following steps: (I) mixing a phosphine oxide derivative represented by formula (1) with a chlorinating agent in a polar organic solvent to cause the reaction between these components; and (II-1) adding a salt of a metal having an ionization tendency equal to or lower than that of aluminum to the reaction mixture and carrying out the reductive reaction in the presence of aluminum or (II-2) subjecting the reaction mixture to electrolytic reduction, thereby producing a phosphine derivative represented by formula (2). $Ar_nR_{3-n}P=O$ (1) $Ar_nR_{3-n}P$ (2) In formulae (1) and (2), Ar represents an aryl group such as a phenyl group, a phenyl group having a substituent, a heteroaromatic ring group, and a heteroaromatic ring group having a substituent; R represents an aliphatic hydrocarbon group or an aliphatic hydrocarbon group having a substituent; and n represents an integer of 0 to 3.

20 Claims, No Drawings

OTHER PUBLICATIONS

Issleib et al., "Zur Reduktion aromatischer Phosphinoxyde mit Lithiumalanat" *Zeitschrift für anorganische und allgemeine Chemie*, vol. 299, pp. 58-68, 1959.

Lecat et al., "Regeneration Electrochimique de la Triphenylphosphine" *Tetrahedron Letters* vol. 28, No. 47, pp. 5821-5822, 1987.

Masaki et al., "Reaction of Tertiary Phosphine Dichlorides with Thiols in the Presence of Triethylamine. A Convenient Method for the Reduction of Phosphine Oxides to Phosphines" *Chemistry Letters*, The Chemical Society of Japan, pp. 151-152, 1977.

Mathey et al., "Reduction des Oxydes de Phosphines par le Systeme $Cp_2TiCl_2$-Mg" *Tetrahedron Letters*, vol. 21, pp. 2525-2526, 1980.

Somasundaram et al., "Photocatalyzed Oxidation of Triphenyl Derivatives of P, As, Sb & Bi and Reduction of Their Oxides" *J. Org. Chem.* vol. 61, No. 8, pp. 2895-2896, 1996.

Yanilkin et al., "Electrochemical deoxygenation of triphenyl phosphine oxide" *Russian Chemical Bulletin* vol. 45, No. 5, pp. 1257-1258, 1996.

Denney et al., "Reaction of Triphenylphosphine Dihalides with Grignard and Organolithium Reagents" *J. Org. Chem.* vol. 32, pp. 3710-3711, 1967.

Griffin et al., "Alane—A Novel Way to Reduce Phosphine Oxides" *Tetrahedron Letters* vol. 39, No. 71, pp. 4405-4406, 1998.

International Search Report for PCT/JP2009/058980 mailed Jun. 16, 2009.

* cited by examiner

PROCESS FOR PRODUCTION OF PHOSPHINE DERIVATIVE FROM PHOSPHINE OXIDE DERIVATIVE

TECHNICAL FIELD

The present invention relates to a method for producing a phosphine derivative represented by the following formula (2), characterized by carrying out a reduction reaction of a phosphine oxide derivative represented by the following formula (1) in a polar organic solvent using a chlorinating agent and a salt of a metal having an ionization tendency equal to or lower than that of aluminum in the presence of aluminum.

In addition, the present invention relates to a method for producing a phosphine derivative represented by the following formula (2), comprising subjecting a phosphine oxide derivative represented by the following formula (1) to electrolytic reduction together with a chlorinating agent.

  (1)

  (2)

In the formulae (1) and (2), Ar represents an aryl group such as a phenyl group, a phenyl group having a substituent, a heteroaromatic ring group, and a heteroaromatic ring group having a substituent; R represents an aliphatic hydrocarbon group or an aliphatic hydrocarbon group having a substituent; and n represents an integer of 0 to 3.

BACKGROUND ART

The phosphine derivative according to the present invention is an important reactant widely used for an organic synthesis reaction such as Wittig reaction or Mitsunobu reaction. In these reactions, phosphine oxide derivatives are generated as a by-product and stored in a repository or the like in large quantities as an intractable waste. If the phosphine oxide derivatives can be reduced by an appropriate method, to convert the derivatives to phosphine derivatives, it allows the regeneration and recycle of the reactant and clears up the disposal problem of the intractable waste described above once for all.

As a reaction example that converts a phosphine oxide derivative to a phosphine derivative, methods where a metal hydride is allowed to act (NON-PATENT DOCUMENT 5) such as a reaction using trichlorosilane as shown by the following equation (3) (NON-PATENT DOCUMENT 1), a reaction using triethoxysilane or polymethylhydrosiloxane as shown by the following equation (4) (NON-PATENT DOCUMENT 2), a reaction using lithium aluminum hydride and cerium chloride as shown by the following equation (5) (NON-PATENT DOCUMENT 3), a reaction using lithium aluminum hydride as shown by the following equation (6) (NON-PATENT DOCUMENT 4), and a reaction using alane as shown by the following equation (7) are reported.

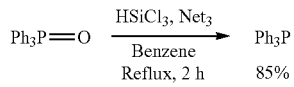  (3)

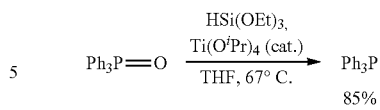  (4)

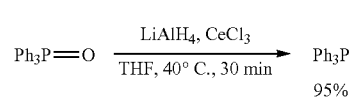  (5)

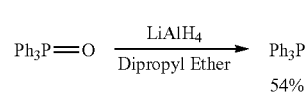  (6)

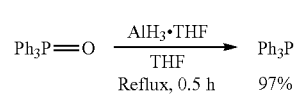  (7)

However, these metal hydrides are all expensive and involve the risk of ignition or the like, and thus extra care is required for handling. Therefore, there is a problem in treating large quantities of phosphine oxide derivatives, from the viewpoint of cost, complex operations and the like.

As another reduction reaction of a triphenylphosphine oxide, a reaction where magnesium metal and titanocene dichloride are allowed to act as shown by the following equation (8) (NON-PATENT DOCUMENT 6), a reaction where samarium iodide is allowed to act as shown by the following equation (9) (NON-PATENT DOCUMENT 7), a reaction where activated carbon and hydrocarbon are allowed to act as shown by the following equation (10) (PATENT DOCUMENT 1), a reaction where a reductant prepared from a bismuth oxide and a titanium oxide is allowed to act as shown by the following equation (11) (PATENT DOCUMENT 2), a reaction where light is allowed to act in the presence of a titanium oxide as shown by the following equation (12) (NON-PATENT DOCUMENT 8), a reaction where silicon powder, chlorosilane, and iron chloride are allowed to act as shown by the following equation (13) (PATENT DOCUMENT 3), and the like are reported. However, these reactions can never be said as a practical method of producing triphenylphosphine, from the viewpoint of cost and safety.

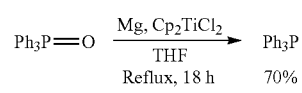  (8)

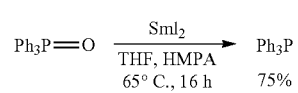  (9)

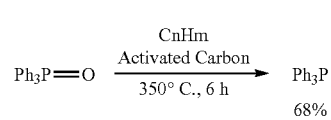  (10)

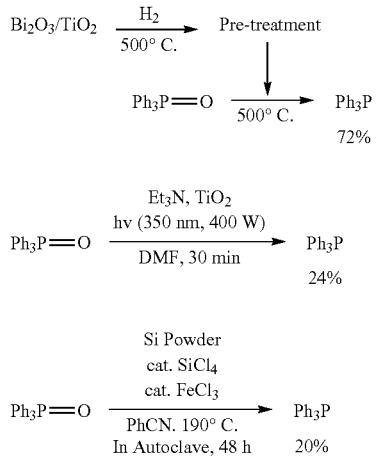

(11)

(12)

(13)

In addition, as for electrolytic reduction of triphenylphosphine oxide, a reaction shown by the following equation (14) (PATENT DOCUMENT 4) is reported.

(14)

$$Ph_3P{=}O \xrightarrow[\substack{tBuOH \\ MeBu_3N^+TsO^- \\ H_2NCH_2CH_2NH_2}]{+e^-} Ph_2P({=}O)H + PhPH_2 + Ph_2PH$$

However, the product is a complex mixture of benzene, cyclohexadiene, cyclohexene, and the like, in addition to diphenylphosphine oxide, phenylphosphine, and diphenylphosphine, and triphenylphosphine is not produced at all.

Furthermore, a method of subjecting triphenylphosphine oxide to electrolytic reduction in acetonitrile in the presence of aluminum chloride using aluminum as an anode to produce triphenylphosphine as shown by the following equation (15) (PATENT DOCUMENT 5 and NON-PATENT DOCUMENT 9), a method of treating a triphenylphosphine oxide derivative with phosphorus pentasulfide and dimethyl sulfate, and thereafter carrying out electrolytic reduction in methanol containing lithium chloride to produce triphenylphosphine as shown by the following equation (16), and a method of treating with methyl trifluoromethanesulfonate, and thereafter carrying out electrolytic reduction in methanol containing tetrabutylammonium trifluoromethanesulfonate to produce triphenylphosphine (PATENT DOCUMENT 10) are reported. However, in the former, the yield of triphenylphosphine is only 11%, and the current efficiency is also 8% or less, and thus it can never be said as a technology for practical use. Also, in the latter, complex operations are necessary for the preparation of a pentavalent phosphorus compound to be subjected to electrolysis, and the yield of the total process including electrolytic reduction is at most 45% or so, and thus it is not satisfactory as a practical method.

(15)

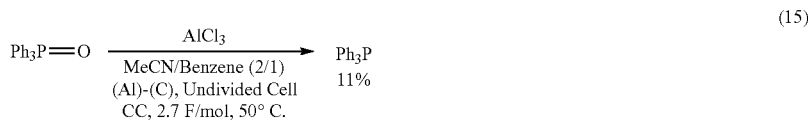

(16)

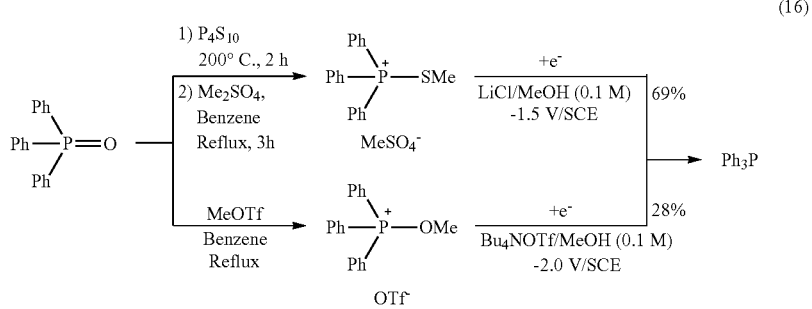

On the other hand, as a two-step method including the steps of once converting triphenylphosphine oxide to one other pentavalent phosphorus compound and reducing this compound to convert the compound to triphenylphosphine, the following equation (17) is reported (NON-PATENT DOCUMENT 11). However, expensive lithium aluminum hydride is used in the reduction reaction of the second step, and thus it is not practical.

(17)

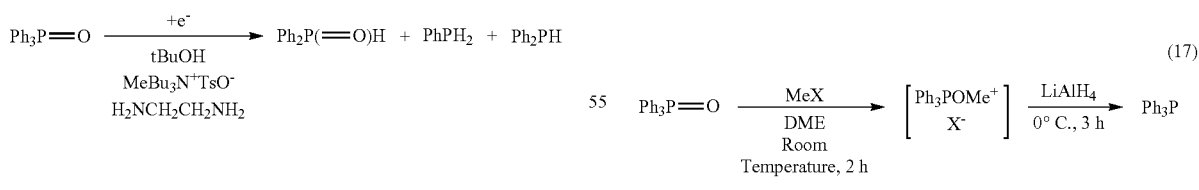

$X^- = TfO^-, TsO^-, MsO^-, I^-$
94-97%

In addition, a method of synthesizing triphenylphosphine represented by the following formula (2) (Ar is a phenyl group) in high yield by a reaction where lithium aluminum hydride or sodium metal is allowed to act on a pentavalent phosphorus compound represented by the following formula (18) (Ar is a phenyl group, X is chlorine) prepared from triphenylphosphine oxide represented by the following formula (1) (Ar is a phenyl group), as shown by the following equation (19), is reported (NON-PATENT DOCUMENT 12).

$$Ar_3P=O \quad (1)$$

$$Ar_3P \quad (2)$$

$$Ar_3PX_2 \quad (18)$$

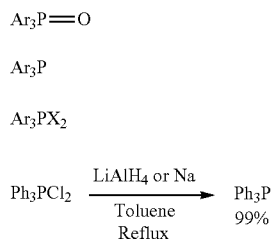   (19)

However, this reaction involves the risk of ignition or the like and uses lithium aluminum hydride or sodium metal that requires extra care for handling, and thus there are many problems as a practical method that treats large quantities of triphenylphosphine oxides.

In addition, as a method of synthesizing triphenylphosphine represented by the following formula (2) from a pentavalent phosphorus compound represented by the following formula (18) (Ar is a phenyl group, X is chlorine), a method where thiophenol is allowed to act as shown by the following equation (20) (NON-PATENT DOCUMENT 13), a method where butyllithium is allowed to act as shown by the following equation (21) (NON-PATENT DOCUMENT 14), a method where phenylmagnesium bromide is allowed to act as shown by the following equation (22) (NON-PATENT DOCUMENT 14), a method where white phosphorus is allowed to act as shown by the following equation (23) (PATENT DOCUMENT 6), a method where silicon powder is allowed to act as shown by the following equation (24) (PATENT DOCUMENT 7), a method where iron powder is allowed to act as shown by the following equation (25) (PATENT DOCUMENT 8), a method where sodium metal and phosphorus trichloride are allowed to act as shown by the following equation (26) (PATENT DOCUMENT 9), and methods such as hydrogenation reactions as shown by the following equations (27) to (32) (PATENT DOCUMENTS 10 to 15) are reported. However, all methods require an expensive reactant in excess amount, strict reaction conditions of high temperature and high pressure or the like, and thus these methods are not fully satisfied as a practical method of reducing the pentavalent phosphorus compound represented by the following formula (18) for practical use.

$$Ar_3P \quad (2)$$

$$Ar_3PX_2 \quad (18)$$

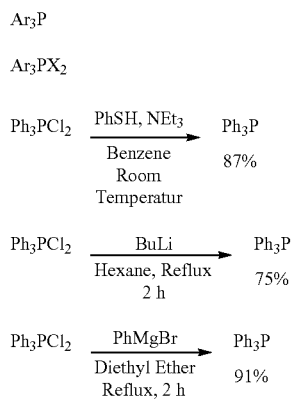

(20)

(21)

(22)

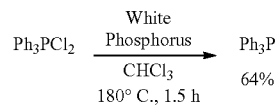 (23)

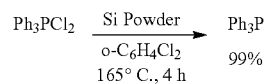 (24)

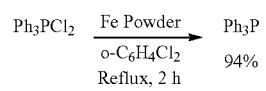 (25)

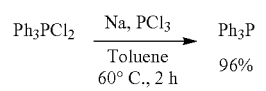 (26)

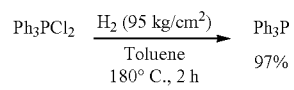 (27)

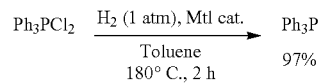 (28)

Mtl = Rh, Pd, Pt

 (29)

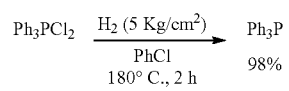 (30)

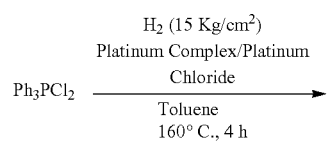 (31)

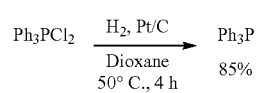 (32)

Also, methods of synthesizing triphenylphosphine represented by the following formula (2) (Ar is a phenyl group) in high yield by reactions where aluminum metal is allowed to act on a pentavalent phosphorus compound represented by the following formula (18) (Ar is a phenyl group, X is chlorine) prepared from triphenylphosphine oxide represented by the following formula (1) (Ar is a phenyl group), as shown by the following equations (33) to (35) are reported (PATENT DOCUMENTS 16 to 18). However, these production methods are all carried out under the reaction conditions of a high temperature at 90° to 180° C., and many methods take a long treatment time of several hours to 20 hours. Aluminum used is preferably in powder form, and those previously made uniform to a proper range of particle diameter (200 to 500 μm) by a sieve are advantageously used. However, not only this adjustment costs much, but also, aluminum in powder form is easy to ignite, and thus extra care is required for handling. In addition, the pentavalent phosphorus compound represented by the following formula (18) (Ar is a phenyl group, X is chlorine) to be subjected to the reaction is prepared by reacting triphenylphosphine oxide with a chlorinating agent such as phosgene, and normally, separation and purification operations are necessary after the reaction, and it is required that the chlorinating agent and a chlorination product generated as a by-product are reduced to within the limits. The reported method of producing a phosphine derivative by the preparation of the pentavalent phosphorus compound represented by the following formula (18) (Ar is a phenyl group, X is chlorine) from a phosphine oxide derivative and the reduction by aluminum metal is not fully satisfactory as a practical method, and the development of the production method suitable for industrialization is anticipated.

  (1)

  (2)

  (18)

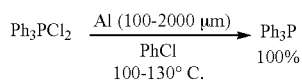  (33)

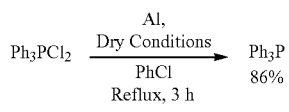  (34)

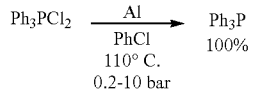  (35)

Prior Art Document

Patent Document
PATENT DOCUMENT 1: JP62-4294 A
PATENT DOCUMENT 2: JP8-225468 A
PATENT DOCUMENT 3: EP0548682, U.S. Pat. No. 5,792,884
PATENT DOCUMENT 4: WO 2005-031040 A2
PATENT DOCUMENT 5: Indian Pat. Appl. 2002DE00793
PATENT DOCUMENT 6: U.S. Pat. No. 3,481,988, DE1247310
PATENT DOCUMENT 7: U.S. Pat. No. 5,792,884, EP548682
PATENT DOCUMENT 8: U.S. Pat. No. 3,780,111
PATENT DOCUMENT 9: U.S. Pat. No. 4,036,889, DE2638720
PATENT DOCUMENT 10: JP53-34725 A
PATENT DOCUMENT 11: JP55-149293 A
PATENT DOCUMENT 12: JP63-26115 B
PATENT DOCUMENT 13: JP55-149294 A
PATENT DOCUMENT 14: JP55-149293 A
PATENT DOCUMENT 15: JP62-56879 B
PATENT DOCUMENT 16: JP7-76592 A
PATENT DOCUMENT 17: U.S. Pat. No. 3,405,180
PATENT DOCUMENT 18: EP0761676, DE19532310
Non-Patent Document
NON-PATENT DOCUMENT 1: Fritzsche, H.; Hasserodt, U.; Korte, F.; Friese, G.; Adrian, K. Chem. Bet 1965, 98, 171-174.
NON-PATENT DOCUMENT 2: Coumbe, T.; Lawrence, N. J.; Muhammad, F. Tetrahedron Lett. 1994, 35, 625-628.
NON-PATENT DOCUMENT 3: Imamoto, T.; Takeyama, T.; Kusumoto, T. Chem. Lett. 1985, 1491-1492.
NON-PATENT DOCUMENT 4: Issleib, K.; Grams, G, Zeitschrift fur Anorganishe and Allgemeine Chemie 1959.299.58-68.
NON-PATENT DOCUMENT 5: Griffin, S.; Heath, L.; Wyatt, P. Tetrahedron Lett. 1998, 39, 4405-4406.
NON-PATENT DOCUMENT 6: Mathey, F.; Maillet, R. Tetrahedron Lett. 1980, 21, 2525-2526.
NON-PATENT DOCUMENT 7: Handa, Y.; Inanaga. J.; Yamaguchi, M. J. Chem. Soc.; Chem. Comm. 1989, 288-289.
NON-PATENT DOCUMENT 8: Somasundaram, N.; Srinivasan, C. J. Org. Chem. 1996, 61, 2895-2896.
NON-PATENT DOCUMENT 9: Yanilkin, V. V.; Gromakov, V. S.; Nigmadzyanov, F. F. Russ. Chem. Bull. 1996, 45, 1257-1258.
NON-PATENT DOCUMENT 10: Lecat, J. L.; Devaud, M. Tetrahedron Lett. 1987, 28, 5821-5822.
NON-PATENT DOCUMENT 11: Imamoto, T.; Kikuchi, S.; Miura, T.; Wada, Y Org. Lett. 2001, 3, 87-90.
NON-PATENT DOCUMENT 12: Horner, L.; Hoffman, H.; Beck, P. Chem. Ber., 1958, 91, 1583-1588.
NON-PATENT DOCUMENT 13: Masaki, M.; Fukui, K. Chem. Lett. 1977, 151-152.
NON-PATENT DOCUMENT 14: Denney, D. B.; Gross, F. J. J. Org. Chem. 1967, 32, 3710-3711.

SUMMARY OF THE INVENTION

Problems to be Solved by the Invention

The establishment of a method for producing a phosphine derivative, which highly selectively converts a phosphine oxide derivative represented by the following formula (1) to a phosphine derivative represented by the following formula (2) in high yield by carrying out reduction by simple operations at a low cost and a low risk and under mild conditions, in other words, a method for regenerating a phosphine derivative from a phosphine oxide derivative, is desired.

  (1)

  (2)

In the formulae (1) and (2), Ar represents an aryl group such as a phenyl group, a phenyl group having a substituent, a heteroaromatic ring group, and a heteroaromatic ring group having a substituent; R represents an aliphatic hydrocarbon group or an aliphatic hydrocarbon group having a substituent; and n represents an integer of 0 to 3.

Means for Solving the Problems

As a result of intensive studies on a method of converting a phosphine oxide derivative represented by the following formula (1) to a phosphine derivative represented by the following formula (2) in order to accomplish the objects described above, the phosphine derivative has been successfully efficiently obtained by subjecting the phosphine oxide derivative to a reduction reaction in a polar organic solvent using a chlorinating agent, aluminum, and a salt of a metal having an ionization tendency equal to or lower than that of aluminum.

In addition, as a result of intensive studies on a method of converting a phosphine oxide derivative represented by the following formula (1) to a phosphine derivative represented by the following formula (2) at once by converting to an activated pentavalent phosphorus compound by a simple pretreatment and directly subjecting the reaction mixture to electrolytic reduction without separation and purification, the phosphine derivative has been successfully efficiently obtained.

$$Ar_nR_{3-n}P=O \quad (1)$$

$$Ar_nR_{3-n}P \quad (2)$$

In the formulae (1) and (2), Ar represents an aryl group such as a phenyl group, a phenyl group having a substituent, a heteroaromatic ring group, and a heteroaromatic ring group having a substituent; R represents an aliphatic hydrocarbon group or an aliphatic hydrocarbon group having a substituent; and n represents an integer of 0 to 3.

More specifically, the present invention is as follows.

[1] A method for producing a phosphine derivative represented by the following formula (2) from a phosphine oxide derivative represented by the following formula (1), comprising the steps of:
 (I) mixing the phosphine oxide derivative with a chlorinating agent in a polar organic solvent, to cause a reaction; and
 (II-1) adding a salt of a metal having an ionization tendency equal to or lower than that of aluminum to the reaction mixture, to carry out a reduction reaction in the presence of aluminum or
 (II-2) subjecting the reaction mixture to electrolytic reduction,
 thereby producing the phosphine derivative:

$$Ar_nR_{3-n}P=O \quad (1)$$

$$Ar_nR_{3-n}P \quad (2)$$

wherein in the formulae (1) and (2), Ar represents an aryl group such as a phenyl group, a phenyl group having a substituent, a heteroaromatic ring group, or a heteroaromatic ring group having a substituent; R represents an aliphatic hydrocarbon group or an aliphatic hydrocarbon group having a substituent; and n represents an integer of 0 to 3.

[2] The method according to [1], wherein the phosphine derivative is produced by the reduction reaction in the (II-1), and when adding the salt of a metal having an ionization tendency equal to or lower than that of aluminum, aluminum is also added to the reaction mixture.

[3] The method according to [1], wherein the phosphine derivative is produced by the reduction reaction in the (II-1), and when mixing the phosphine oxide derivative with the chlorinating agent in the polar organic solvent, aluminum is also mixed.

[4] The method according to any of [1] to [3], wherein the chlorinating agent is any of oxalyl chloride, phosgene, diphosgene, and thionyl chloride.

[5] The method according to any of [1] to [4], wherein the phosphine oxide derivative is used in an amount of 5 to 50% by mass of the polar organic solvent.

[6] The method according to any of [1] to [5], wherein the phosphine derivative is produced by the reduction reaction in the (II-1), and aluminum is used in an amount of 0.66 to 5 mol based on 1 mol of the phosphine oxide derivative.

[7] The method according to any of [1] to [6], wherein the phosphine derivative is produced by the reduction reaction in the (II-1), and the salt of a metal is a salt of a metal having an ionization tendency equal to or lower than that of tin.

[8] The method according to any of [1] to [6], wherein the phosphine derivative is produced by the reduction reaction in the (II-1), and a chloride, a bromide, an iodide, a perchlorate, a sulfate, or a nitrate of a metal from groups 4 to 15 of the periodic table is used as the salt of a metal having an ionization tendency equal to or lower than that of aluminum.

[9] The method according to any of [1] to [7], wherein the phosphine derivative is produced by the reduction reaction in the (II-1), and the salt of a metal is a chloride or bromide of a metal having an ionization tendency equal to or lower than that of tin.

[10] The method according to any of [1] to [9], wherein the phosphine derivative is produced by the reduction reaction in the (II-1), and the salt of a metal having an ionization tendency equal to or lower than that of aluminum is used in an amount of 0.0001 to 1 mol based on 1 mol of aluminum.

[11] The method according to any of [1] to [10], wherein the polar organic solvent is an aprotic polar organic solvent.

[12] The method according to any of [1] to [11], wherein the polar organic solvent is acetonitrile or a mixed solvent comprising acetonitrile as a main solvent.

[13] The method according to any of [1] to [12], wherein the phosphine derivative is produced by the reduction reaction in the (II-1), and at that time, the reduction reaction is carried out in the presence of excess aluminum, and the phosphine oxide derivative, the chlorinating agent, and the polar organic solvent are further added to the aluminum collected after the reduction reaction, to produce the phosphine derivative.

[14] A method for producing a triarylphosphine derivative represented by the following formula (37), comprising subjecting a mixture of a triaryl phosphine oxide derivative represented by the following formula (36) with a chlorinating agent to electrolytic reduction in a polar organic solvent:

$$Ar_3P=O \quad (36)$$

wherein, Ar represents an aryl group such as a phenyl group, a phenyl group having a substituent such as p-methyl or p-methoxy, or a heteroaromatic ring group such as a 2-pyridyl group, a 3-pyridyl group, or a 3-thienyl group;

$$Ar_3P \quad (37)$$

wherein, Ar represents an aryl group such as a phenyl group, a phenyl group having a substituent such as p-methyl or p-methoxy, or a heteroaromatic ring group such as a 2-pyridyl group, a 3-pyridyl group, or a 3-thienyl group.

[15] A method for producing a triarylphosphine derivative represented by the following formula (37) from a triaryl phosphine oxide derivative represented by the following formula (36), comprising the steps of:
 mixing the triaryl phosphine oxide derivative with a chlorinating agent in a polar organic solvent, to cause a reaction; and
 adding a salt of a metal having an ionization tendency equal to or lower than that of aluminum to the reaction mixture to carry out a reduction reaction, thereby producing the triarylphosphine derivative,
 wherein the reduction reaction is carried out in the presence of aluminum:

$$Ar_3P=O \quad (36)$$

$$Ar_3P \quad (37)$$

wherein in the formulae (36) and (37), Ar represents an aryl group such as a phenyl group, a phenyl group having a substituent, a heteroaromatic ring group, or a heteroaromatic ring group having a substituent.

Effects of the Invention

The production method of the present invention does not need to use an expensive compound and a compound having a problem in safety in a step of converting a phosphine oxide derivative to a phosphine derivative and does not also need to go through a high pressure and a high temperature. Therefore, a phosphine derivative can be industrially produced at a low cost in a safe and simple manner.

More specifically, in the conventional production method, it has been necessary, first, to prepare a phosphine dichloride derivative by reacting a chlorinating agent such as phosgene to a phosphine oxide derivative, purify and isolate the resulting phosphine dichloride derivative, and thereafter subject the product to a reduction reaction, thereby synthesizing a phosphine derivative. The reason why the purification and isolation operations are necessary is that a chlorinating agent and a chlorination product generated as a by-product are necessary to be reduced to within the limits, and also, the conventional method has required a long time for operations and caused reduction of the yield. On the other hand, the production method of the present invention is not affected by a chlorinating agent and a chlorination product generated as a by-product in the reduction reaction. Therefore, the reaction mixture can be directly subjected to a reduction reaction without purifying and isolating a phosphine dichloride derivative from the reaction mixture produced in a chlorination reaction, and thus the time for operation can be shortened, and the yield can be increased.

Also, the conventional methods of synthesizing a phosphine derivative from a phosphine dichloride derivative have been all carried out under the reaction conditions of a high temperature of 90° to 180° C., and many methods have taken a long treatment time of several hours to 20 hours. On the other hand, in the method of the present invention, the reaction can be carried out at a lower temperature (e.g. room temperature) in a shorter time (e.g. 10 minutes or so), as compared to the conventional technology. Furthermore, in the conventional method, it has been necessary to use aluminum in powder form previously made uniform to a proper range of particle diameter (200 to 500 μm) by a sieve. However, aluminum in powder form not only costs much in adjusting the particle diameter but also is easy to ignite, and thus extra care is required for handling. On the other hand, according to the production method of the present invention, there is less restriction on the shape and particle diameter of aluminum, for example, aluminum foil can be used, and thus it is very easy for handling.

As described above, according to the production method of the present invention, chlorination treatment and reduction reaction from a phosphine oxide derivative can be carried out at a lower temperature in a shorter time as compared to the conventional technology and industrially advantageously carried out by using aluminum and a salt of a metal having an ionization tendency equal to or lower than that of aluminum, without using a high-risk chemical. Furthermore, since it is not necessary to purify and isolate the reaction intermediate product (phosphine dichloride derivative), high-yield production is possible. Moreover, it is also possible to carry out whole reaction in a one pot (one reactor), whereby the reaction can be industrially very advantageously carried out.

Furthermore, in the production method of the present invention, the first reaction is carried out using excess aluminum, and aluminum being present as a solid is separated and collected from the reaction solution by a method of filtration or the like, and the second reaction and after can be also further carried out using the collected aluminum. As described above, the reaction is carried out repeatedly using the collected aluminum, whereby the second reaction and after can be carried out, and thus the reaction can be industrially advantageously carried out.

In addition, simple pre-treatment and electrolytic reduction are carried out, whereby a phosphine derivative can be industrially produced from a phosphine oxide derivative cheaply and safely.

Mode for Carrying Out the Invention

As one embodiment for carrying out the present invention, the production method of producing a phosphine derivative represented by the following formula (2) including the step of adding aluminum and a salt of a metal having an ionization tendency equal to or lower than that of aluminum to the reaction mixture prepared by mixing a phosphine oxide derivative represented by the following formula (1) with a chlorinating agent in a polar organic solvent to carry out the reaction will be described.

It is assumed herein that an aryl group (Ar) of the phosphine oxide derivative represented by the following formula (1) and the phosphine derivative represented by the following formula (2) includes a phenyl group, a phenyl group having a substituent, a heteroaromatic ring group, and a heteroaromatic ring group having a substituent. Examples of the aryl group include a phenyl group, phenyl groups having a substituent that does not change under the chlorination and reduction conditions, and further, heteroaromatic ring groups such as a 2-pyridyl group, a 3-pyridyl group, a 3-thienyl group, and a 2-furyl group, and heteroaromatic ring groups having a substituent. Examples of such a substituent include substituents such as p-methyl, p-methoxy, o-methyl, p-fluoro, p-chloro, and p-phenyl.

Next, it is assumed that an aliphatic hydrocarbon group (R) is an aliphatic hydrocarbon group such as an alkyl group, an alkenyl group or an alkynyl group and includes those having a substituent.

n is an integer of 0 to 3, and triarylphosphine oxides with n being 3 or diarylalkylphosphine oxides with n being 2 are preferably used, and specifically, triphenylphosphine oxide, tri(p-tolyl)phosphine oxide, tri(m-tolyl)phosphine oxide, tri (o-tolyl)phosphine oxide, tri(p-methoxyphenyl)phosphine oxide, tri(p-chlorophenyl)phosphine oxide, tri(2-furyl)phosphine oxide, diphenylmethylphosphine oxide, and diphenylethylphosphine oxide are preferably used, and triphenylphosphine oxide is most preferably used.

$$Ar_nR_{3-n}P=O \qquad (1)$$

$$Ar_nR_{3-n}P \qquad (2)$$

The chlorinating agent used in the present invention includes oxalyl chloride, phosgene, diphosgene, thionyl chloride, phosphoryl chloride, phosphorus pentachloride, perchlorobutanoyl chloride, dichlorobenzodioxol, N,N-dimethylchlorom ethylimmonium chloride, or N,N-diethylchlorom ethylimmonium chloride. Among these, the chlorinating agents that generate only gas as a by-product from a chlorination reaction are preferably used, and specifically, oxalyl chloride, phosgene, diphosgene or thionyl chloride are more preferably used. An equivalent molar amount or 1.01 to 1.1 mol of the chlorinating agent based on a mole of the phosphine oxide derivative is added, and the mixture is stirred at 0° to 80° C. for 1 minute to 1 hour, and thereafter a reduction reaction of a next reaction step is carried out. Preferably, an equivalent molar amount of oxalyl chloride is added as the chlorinating agent, and the mixture is stirred at 0° to 30° C. for 1 to 10 minutes and can thereafter proceed to the next reaction step. The phosphine oxide derivative is used at this time in an amount of 5 to 50% by mass and preferably 15 to 35% by mass of the polar organic solvent. A polar organic solvent is used as a solvent used in this reaction step and next reduction reaction. The polar organic solvent refers to an organic solvent having a high permittivity. Those having a relative permittivity at 20° C. of 2 or more are preferably used, and those having a relative permittivity at 20° C. of 10 or more are more preferably used. Specific polar organic solvent includes acetonitrile, butyronitrile, N,N-dimethylformamide, N-methylpiperidone, pyridine, chlorobenzene, chloroform, dichloromethane, propionitrile, and the like, and acetonitrile or a mixed solvent comprising acetonitrile as a main solvent is preferably used. Examples of a solvent used for the mixed solvent with acetonitrile include organic solvents such as N,N-dimethylformamide, N-methylpiperidone, pyridine, tetrahydrofuran, dioxane, benzene, chlorobenzene, toluene, dichloromethane, chloroform, acetone, ethyl methyl ketone, and diethyl ether. The ratio of acetonitrile to an organic solvent added in the mixed solvent is normally 1:0.3 to 1:0.001, and preferably 1:0.1 to 1:0.01.

It is a characteristic of the present invention that the reduction reaction of the next reaction step is carried out under environmental conditions of ordinary temperature and ordinary pressure. The reaction temperature is not particularly limited, but is preferably in the range of 0° to 100° C. and more preferably 0° to 40° C. Aluminum is used this time in an amount of 0.66 to 100 mol and more preferably 1 to 5 mol based on 1 mol of the phosphine oxide derivative. The shape of aluminum may be any of rod-shaped, platy, foil, granular, powdery, ribbon-shaped and spherical, and shredded aluminum foil or granular aluminum that is easy for handling is preferably used. Also, examples of the metal salt of having an ionization tendency equal to or lower than that of aluminum used include chlorides, bromides, iodides, nitrates, perchlorates and sulfates of lead, tin, bismuth, aluminum, nickel, iron, cobalt, zinc, and the like, and specific examples include lead (II) bromide, lead(II) chloride, lead(II) nitrate, bismuth(III) bromide, tin(II) chloride, tin(IV) chloride, nickel(II) bromide, iron(III) chloride, iron(III) perchlorate, zinc(II) bromide, and copper(II) sulfate; the metal salt is not particularly limited as long as it is a salt of a metal having an ionization tendency equal to or lower than that of aluminum. A salt of a metal having an ionization tendency equal to or lower than that of aluminum is preferably used, and a bromide or a chloride of lead, tin or bismuth is further preferably used. The amount of this salt of a metal having an ionization tendency equal to or lower than that of aluminum is used in an amount of 0.0001 to 1 mol and more preferably 0.001 to 0.01 mol based on 1 mol of aluminum. The period of the reduction reaction started by the addition of the salt of a metal having an ionization tendency equal to or lower than that of aluminum is not constant depending on the reaction conditions and is from 1 minute to 3 hours, and more preferably from 5 minutes to 30 minutes.

While aluminum is an essential component when the salt of a metal having an ionization tendency equal to or lower than that of aluminum is added to cause a reaction, aluminum is not involved in the reaction by the chlorinating agent, that is the previous step thereof. Therefore, as another embodiment for carrying out the present invention, it is also possible to charge a phosphine oxide derivative, aluminum and a polar organic solvent into a reactor, adding a chlorinating agent thereto to cause a reaction, and subsequently adding a salt of a metal having an ionization tendency equal to or lower than that of aluminum to this reaction mixture to cause a reaction.

In this case, aluminum stably exists in the reaction mixture until the reaction is started by adding the salt of a metal having an ionization tendency equal to or lower than that of aluminum.

From the reaction mixture obtained by the reduction reaction as described above, a phosphine derivative is obtained by separation and purification according to the conventionally known methods such as solvent extraction and recrystallization. The reaction mixture contains aluminum chloride and a metal salt having an ionization tendency equal to or lower than that of aluminum, and these substances need to be removed by purification. The content of aluminum chloride in the phosphine derivative after purification is preferably 10 ppm or less, and further preferably 1 ppm or less. The content of the metal salt having an ionization tendency equal to or lower than that of aluminum after purification is preferably 1 ppm or less, and further preferably substantially 0 ppm.

In addition, in the present invention, as described above, in producing the phosphine derivative from the phosphine oxide derivative, it is possible to carry out the reaction using excess aluminum (first reaction), separate and collect aluminum that exists as a solid from the reaction solution by a method of filtration or the like, further produce the phosphine derivative from the phosphine oxide derivative using the collected aluminum, and repeat this process (second reaction and after). In this case, in the second reaction and after, it is not necessary to use a salt of a metal having an ionization tendency equal to or lower than that of aluminum. As described above, the reaction progression without adding a salt of a metal having an ionization tendency equal to or lower than that of aluminum in the second reaction and after shows that, once aluminum is activated by a salt of a metal having an ionization tendency equal to or lower than that of aluminum, the activated state of aluminum in the system continues even repeatedly carrying out the reaction.

The "excess" described above refers to the use of aluminum in an amount of normally twice or more and 5,000 times or less and preferably 5 times or more and 500 times or less based on the theoretical amount of aluminum used in the reaction. Incidentally, the theoretical amount of aluminum in the reaction is 0.67 mol based on 1 mol of the phosphine oxide derivative.

As described above, the reaction is repeatedly carried out using the collected aluminum, whereby the second reaction and after can be efficiently carried out and can be industrially advantageously carried out.

Next, the production method of producing a phosphine derivative represented by the formula (2), including the step of subjecting a phosphine oxide derivative represented by the formula (1) to electrolytic reduction together with a chlorinating agent, which is an another embodiment for carrying out the present invention, will be described.

It is assumed herein that an aryl group (Ar) of the phosphine oxide derivative represented by the following formula (1) and the phosphine derivative represented by the following formula (2) includes a phenyl group, a phenyl group having a substituent, a heteroaromatic ring group, and a heteroaromatic ring group having a substituent. Examples of the aryl group include a phenyl group, phenyl groups having a substituent that does not change under the electrolytic reduction conditions, and further, heteroaromatic ring groups such as a 2-pyridyl group, a 3-pyridyl group, a 3-thienyl group, and a 2-furyl group, and heteroaromatic ring groups having a substituent. Examples of such a substituent include p-methyl, p-methoxy, o-methyl, p-fluoro, p-chloro, and p-phenyl.

Next, it is assumed that an aliphatic hydrocarbon group (R) is an aliphatic hydrocarbon group such as an alkyl group, an alkenyl group and an alkynyl group and includes those having a substituent.

n is an integer of 0 to 3, and triarylphosphine oxides with n being 3 or diarylalkylphosphine oxides with n being 2 are preferably used, and specifically, triphenylphosphine oxide, tri(p-tolyl)phosphine oxide, tri(m-tolyl)phosphine oxide, tri(o-tolyl)phosphine oxide, tri(p-methoxyphenyl)phosphine oxide, tri(p-chlorophenyl)phosphine oxide, tri(2-furyl)phosphine oxide, diphenylmethylphosphine oxide and diphenylethylphosphine oxide are preferably used, and triphenylphosphine oxide is most preferably used.

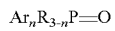 (1)

 (2)

The chlorinating agent used in the present invention includes oxalyl chloride, phosgene, diphosgene, thionyl chloride, phosphoryl chloride, phosphorus pentachloride, perchlorobutanoyl chloride, dichlorobenzodioxol, N,N-dimethylchloromethylimmonium chloride or N,N-diethylchloromethylimmonium chloride. Among these, the chlorinating agents that generate only gas as a by-product from a chlorination reaction are preferably used, and specifically, oxalyl chloride, phosgene, diphosgene or thionyl chloride are more preferably used. An equivalent molar or slightly excess amount of chlorinating agent is added to the phosphine oxide derivative, and the mixture is mixed at 0° to 80° C. for 1 minute to 1 hour, and thereafter electrolysis is carried out. It is preferred that an equivalent molar amount of oxalyl chloride be added as the chlorinating agent, and the mixture is mixed at room temperature for 1 to 2 minutes, and thereafter electrolysis is carried out.

As an electrolytic cell used for electrolytic reduction according to the present invention, a divided cell in which an anode chamber and a cathode chamber are divided by a diaphragm is used, and as more preferable electrolytic cell, a simple undivided cell with a reactive metal as an anode is used. As the reactive metal, a metal eluted as a metal cation by electrolysis is used. Specifically, a metal such as aluminum, magnesium, tin, nickel, zinc or iron or an alloy thereof is used, and aluminum is preferable. Also, a cathode is not particularly limited, and commercially available various metal electrodes and carbon electrodes can be used.

As a solvent used for electrolytic reduction, a polar organic solvent containing or not containing various supporting electrolytes is used. The polar organic solvent refers to an organic solvent having a high permittivity. Those having a relative permittivity at 20° C. of 2 or more are preferably used, and those having a relative permittivity at 20° C. of 10 or more are more preferably used. Specific polar organic solvent includes acetonitrile, butyronitrile, N,N-dimethylformamide, N-methylpiperidone, pyridine, chlorobenzene, chloroform, dichloromethane, and propionitrile, and acetonitrile or a mixed solvent comprising acetonitrile as a main solvent is preferably used. As a solvent used for the mixed solvent with acetonitrile, organic solvents such as N,N-dimethylformamide, N-methylpiperidone, pyridine, tetrahydrofuran, dioxane, benzene, chlorobenzene, toluene, dichloromethane, chloroform, acetone, ethyl methyl ketone and diethyl ether can be exemplified. The ratio of acetonitrile to an organic solvent added in the mixed solvent is normally 1:0.3 to 1:0.001, and preferably 1:0.1 to 1:0.01.

A supporting electrolyte is not always necessary and can be properly added for efficient passage of electricity. The supporting electrolyte is not particularly limited, and a quaternary ammonium salt such as tetra-n-butylammonium tetrafluoroborate, tetra-n-butylammonium perchlorate, tetra-n-butylammonium hexafluorophosphate, tetra-n-butylammonium bis-triflimide, tetra-n-butylammonium bromide or tetraphenylammonium bromide or a metal salt such as lithium iodide, lithium bromide, lithium tetrafluoroborate, sodium perchlorate, aluminum chloride or aluminum bromide is used.

Electrolytic reduction can be carried out under environmental conditions of ordinary temperature and ordinary pressure, and the reaction temperature is preferably in the range of 0° to 50° C. Electrolytic reduction can be carried out under either constant current or constant potential. From the viewpoint of ease of reaction operations or unnecessity of complex apparatus, it is preferred that electrolysis be carried out under constant current. Electrolysis can be carried out at a current density in the range of 0.1 mA/cm$^2$ to 1,000 mA/cm$^2$ and is carried out preferably in the range of 1 mA/cm$^2$ to 200 mA/cm$^2$. The amount of electricity passed depends on the structures of the phosphine oxide derivative used and the chlorinating agent added or electrolytic reduction conditions, and electricity is passed at 1 to 10 F and preferably at 2 to 5 F per 1 mol of the phosphine oxide derivative.

EXAMPLES

Hereinafter, the present invention will be described with reference to Examples, but the present invention is not limited to these Examples.

Example 1

Triphenylphosphine oxide (1.405 g, 5.0 mmol) and acetonitrile (5 mL) were weighted out into a reactor, then oxalyl chloride (0.43 mL, 5.05 mmol) was added thereto under room temperature, and the mixture was stirred for 10 minutes. Then, previously shredded aluminum foil (135 mg, 5.0 mmol) and lead bromide (18 mg, 0.05 mmol) were added to this reaction solution, and subsequently the mixture was stirred for 1 hour under room temperature to cause a reaction. The reaction solution was poured into an iced 5% hydrochloric acid aqueous solution from the reactor, to terminate the reaction, and thereafter the organic layer was separated, and the water layer was extracted with ethyl acetate for 3 times. The organic layers were combined into one, washed with saturated saline, dried on sodium sulfate and concentrated under reduced pressure. The residue was purified with a silica gel column chromatography to give triphenylphosphine (1.189 g, 4.5 mmol, yield: 90%) and triphenylphosphine oxide (128 mg, 0.45 mmol, collection rate: 9%).

Example 2

Triphenylphosphine oxide (1.40 g, 5.0 mmol), shredded aluminum foil (136 mg, 5.0 mmol) and acetonitrile (5 mL) were weighted out into a reactor, then oxalyl chloride (0.46 mL, 5.1 mmol) was added thereto under room temperature, and the mixture was stirred at the same temperature for 10 minutes. Subsequently, lead bromide (18 mg, 0.05 mmol) was added to this reaction solution, and the mixture was stirred for 30 minutes at room temperature. Thereafter, the reaction solution was poured into an iced 5% hydrochloric acid aqueous solution from the reactor, to terminate the reaction. The organic layer was separated, and the water layer was extracted with ethyl acetate for 3 times. The organic layers were combined into one, washed with saturated saline, dried on sodium sulfate and concentrated under reduced pressure.

The residue was purified with a silica gel column chromatography to give triphenylphosphine (1,162 mg, 4.4 mmol, yield: 88%) and triphenylphosphine oxide (21 mg, 0.07 mmol, collection rate: 2%).

Comparative Example 1

Triphenylphosphine oxide (1.405 g, 5.0 mmol) and acetonitrile (5 mL) were weighted out into a reactor, then oxalyl chloride (0.43 mL, 5.05 mmol) was added thereto under room temperature, and the mixture was stirred for 10 minutes. Then, previously shredded aluminum foil (135 mg, 5.0 mmol) was added to this reaction solution, and subsequently the mixture was stirred for 1 hour under room temperature to cause a reaction. The reaction solution was poured into an iced 5% hydrochloric acid aqueous solution from the reactor, to terminate the reaction, and thereafter the organic layer was separated, and the water layer was extracted with ethyl acetate for 3 times. The organic layers were combined into one, washed with saturated saline, dried on sodium sulfate and concentrated under reduced pressure. The residue was purified with a silica gel column chromatography to give triphenylphosphine (47 mg, 0.18 mmol, yield: 4%) and triphenylphosphine oxide (1.32 g, 4.75 mmol, collection rate: 94%).

Examples 3 to 17

Reduction reactions from triphenylphosphine oxide to triphenylphosphine were carried out in the same manner under the same reaction conditions as in Example 1 except for using salts of a metal having an ionization tendency equal to or lower than that of aluminum (catalysts), the amounts added and the reaction times shown in Table 1.

TABLE 1

| | Catalyst | Amount Added (% by mol) | Reaction Time (hours) | Yield (%) Triphenyl-phosphine | Raw Material Collection |
|---|---|---|---|---|---|
| Example 1 | PbBr$_2$ | 1 | 1 | 90 | 9 |
| Example 3 | PbCl$_2$ | 2 | 1 | 98 | 1 |
| Example 4 | SnCl$_2$ | 2 | 1 | 97 | 2 |
| Example 5 | SnBr$_2$ | 2 | 1 | 95 | 4 |
| Example 6 | SnCl$_4$ | 2 | 1 | 96 | 2 |
| Example 7 | BiCl$_3$ | 2 | 1 | 67 | 31 |
| Example 8 | AlCl$_3$ | 20 | 24 | 51 | 35 |
| Example 9 | NiCl$_2$ | 10 | 24 | 43 | 38 |
| Example 10 | NiBr$_2$ | 5 | 24 | 46 | 42 |
| Example 11 | FeCl$_3$ | 5 | 24 | 46 | 42 |
| Example 12 | FeBr$_3$ | 5 | 24 | 24 | 73 |
| Example 13 | Fe(NO$_3$)$_3$ | 5 | 20 | 53 | 43 |
| Example 14 | Fe(ClO$_4$)$_3$ | 5 | 20 | 39 | 54 |
| Example 15 | CoCl$_2$ | 10 | 24 | 24 | 73 |
| Example 16 | ZnBr$_2$ | 30 | 25 | 53 | 43 |
| Example 17 | ZnCl$_2$ | 25 | 24 | 39 | 54 |

Yields were calculated from isolated yield amounts after purifying with a silica gel column chromatography.

Examples 18 to 22

Reduction reactions from triphenylphosphine oxide to triphenylphosphine were carried out in the same manner under the same reaction conditions as in Example 1 except for using solvents shown in Table 2.

TABLE 2

| | Solvent | Yield (%) Triphenyl-phosphine | Raw Material Collection |
|---|---|---|---|
| Example 18 | Propionitrile | 83 | 15 |
| Example 19 | Chlorobenzene | 77 | 22 |
| Example 20 | Chloroform | 78 | 18 |
| Example 21 | Dichloromethane | 63 | 32 |
| Example 22 | Acetonitrile/Diethyl Ether (1/0.05) | 65 | 33 |

Yields were calculated from isolated yield amounts after purifying with a silica gel column chromatography.

Examples 23 to 27

Reduction reactions from triphenylphosphine oxide to triphenylphosphine were carried out in the same manner under the same reaction conditions as in Example 1 except for using aluminum in the forms shown in Table 3 in place of previously shredded aluminum foil.

TABLE 3

| | Form of Aluminum | Yield (%) Triphenyl-phosphine | Raw Material Collection |
|---|---|---|---|
| Example 23 | Spherical (3 mm in Diameter) | 92 | 5 |
| Example 24 | Powdery (0.1 mm in Diameter) | 94 | 3 |
| Example 25 | Platy (0.50 mm) | 90 | 6 |
| Example 26 | Rod-shaped (4 mm in Diameter) | 91 | 5 |
| Example 27 | Ribbon-shaped (0.50 mm × 3.0 mm) | 92 | 4 |

Yields were calculated from isolated yield amounts after purifying with a silica gel column chromatography.

Examples 28 to 33

Reduction reactions were carried out in the same manner under the same reaction conditions as in Example 1 except for using phosphine oxides shown in Table 4 in place of triphenylphosphine oxide.

TABLE 4

| | Phosphine Oxide | Yield (%) Phosphine | Raw Material Collection |
|---|---|---|---|
| Example 28 | Tri(p-tolyl)phosphine Oxide | 95 | 3 |
| Example 29 | Tri(m-tolyl)phosphine Oxide | 92 | 5 |
| Example 30 | Tri(o-tolyl)phosphine Oxide | 90 | 8 |
| Example 31 | Tri(p-methoxyphenyl)phosphine Oxide | 97 | 2 |
| Example 32 | Tri(p-chlorophenyl)phosphine Oxide | 95 | 4 |
| Example 33 | Tri(2-furyl)phosphine Oxide | 90 | 8 |

Yields were calculated from isolated yield amounts after purifying with a silica gel column chromatography.

Example 34

Triphenylphosphine oxide (1.40 g, 5.0 mmol), granular aluminum (spherical, φ=3 mm, 2.13 g, 78.9 mmol) and acetonitrile (5 mL) were weighted out into a reactor, then oxalyl chloride (0.46 mL, 5.10 mmol) was added thereto under room temperature, and the mixture was stirred for 10 minutes. Then, lead bromide (17 mg, 0.05 mmol) was added to this reaction solution, and the mixture was stirred for 1 hour under room temperature to cause a reaction. The reaction solution was taken out with a syringe and poured into an iced 5% hydrochloric acid aqueous solution, and further, the granular aluminum was washed with ethyl acetate, and a wash liquid was also poured into the iced 5% hydrochloric acid aqueous solution as well. The organic layer was separated, and the water layer was extracted with ethyl acetate for 3 times. The organic layers were combined into one, washed with saturated saline, dried on sodium sulfate and concentrated under reduced pressure. The residue was purified with a silica gel column chromatography to give triphenylphosphine (1.26 g, 4.82 mmol, yield: 96%) and triphenylphosphine oxide (28 mg, 0.10 mmol, collection rate: 2%) (first reaction).

Triphenylphosphine oxide (1.401 g, 5.0 mmol) and acetonitrile (5 mL) were weighted out into a reactor containing the granular aluminum collected after the first reaction, then oxalyl chloride (0.46 mL, 5.10 mmol) was added thereto under room temperature, and the mixture was stirred for 1 hour to cause a reaction. The reaction solution was taken out with a syringe and poured into an iced 5% hydrochloric acid aqueous solution, and further, the granular aluminum was washed with ethyl acetate, and a wash liquid was also poured into the iced 5% hydrochloric acid aqueous solution as well. The organic layer was separated, and the water layer was extracted with ethyl acetate for 3 times. The organic layers were combined into one, washed with saturated saline, dried on sodium sulfate and concentrated under reduced pressure. The residue was purified with a silica gel column chromatography to give triphenylphosphine (1.23 g, 4.67 mmol, yield: 93%) and triphenylphosphine oxide (40 mg, 0.14 mmol, collection rate: 3%) (second reaction).

Triphenylphosphine oxide (1.40 g, 5.0 mmol) and acetonitrile (5 mL) were weighted out into a reactor containing the granular aluminum collected after the second reaction, then oxalyl chloride (0.46 mL, 5.10 mmol) was added thereto under room temperature, and the mixture was stirred for 1 hour to cause a reaction. The reaction solution was taken out with a syringe and poured into an iced 5% hydrochloric acid aqueous solution, and further, the aluminum granules were washed with ethyl acetate, and a wash liquid was also poured into the iced 5% hydrochloric acid aqueous solution as well. The organic layer was separated, and the water layer was extracted with ethyl acetate for 3 times. The organic layers were combined into one, washed with saturated saline, dried on sodium sulfate and concentrated under reduced pressure. The residue was purified with a silica gel column chromatography to give triphenylphosphine (1.22 g, 4.63 mmol, yield: 92%) and triphenylphosphine oxide (10 mg, 0.04 mmol, collection rate: 0.7%) (third reaction).

Example 35

1.39 g of triphenylphosphine oxide (5.0 mmol) was weighted out into a glass vessel, then acetonitrile (3 mL) and oxalyl chloride (0.43 mL) were added thereto, and the mixture was stirred for 1 to 2 minutes. Next, tetrabutylammonium trifluoromethanesulfonate (196 mg, 0.5 mmol) was added thereto, and thereafter, an aluminum electrode (anode, 1.5× 1.0 cm$^2$) and a platinum electrode (cathode, 1.5×1.0 cm$^2$) were immersed in the reaction solution, and constant-current electrolysis was carried out at 50 mA while stirring. An electricity of 3 F/mol was applied to triphenylphosphine oxide (8 hours), and thereafter, the mixed solution after the reaction was added to an iced 5% hydrochloric acid aqueous solution, and the mixture was shaken up well and extracted with ethyl acetate. The extracts were combined into one, washed with saturated saline, dried on sodium sulfate and then concentrated under reduced pressure. As a result of analyzing a residue with a gas chromatography, it was revealed that triphenylphosphine was produced at a yield of 85% and 6% of triphenylphosphine oxide was collected.

Gas chromatography conditions: column, SE-52; 5% Chromosorb W (manufactured by Shimadzu Corporation), 3.2 mm×2.1 m, 80-100 mesh; carrier gas, $N_2$ gas; retention time of triphenylphosphine, 25.2 minutes; retention time of triphenylphosphine oxide, 29.6 minutes; retention time of internal standard substance 1,4-diisopropylbenzene, 8.1 minutes Examples 36 to 43

Electrolytic reductions were carried out in the same manner as in Example 35 except for using supporting electrolytes shown in Table 5.

TABLE 5

Study of Supporting Electrolyte

| | | Yield (%)[a] | |
|---|---|---|---|
| | Supporting Electrolyte | Triphenyl-phosphine | Raw Material Collection |
| Example 36 | Bu$_4$NBF$_4$ | 76 | 10 |
| Example 37 | Bu$_4$NPF$_6$ | 91 | 6 |
| Example 38 | Bu$_4$NClO$_4$ | 70 | 9 |
| Example 39 | Bu$_4$NTf$_2$N | 77 | 8 |
| Example 40 | Bu$_4$NBr | 84 | 4 |
| Example 41 | Ph$_4$PBr | 81 | 11 |
| Example 42 | LiBF$_4$ | 86 | 11 |
| Example 43 | AlCl$_3$ | 65 | 21 |

[a]Yields were measured by detection by gas chromatography.

1,4-diisopropylbenzene was used as an internal standard substance.

Examples 44 to 46

Electrolytic reductions were carried out in the same manner as in Example 35 except for supporting electrolytes and electrode materials shown in Table 6.

TABLE 6

Study of Supporting Electrolyte and Electrode Material

| | | Electrode Material | Yield (%)[a] | |
|---|---|---|---|---|
| | Supporting Electrolyte | (Anode)-(Cathode) | Triphenyl-phosphine | Raw Material Collection |
| Example 44 | Bu$_4$NOTf | (Aluminum)-(Graphite Carbon) | 72 | 12 |
| Example 45 | Bu$_4$NOTf | (Magnesium)-(Platinum) | 76 | 20 |
| Example 46 | Ph$_4$PBr | (Aluminum)-(Carbon Felt) | 89 | 4 |

[a]Yields were measured by detection by gas chromatography.

1,4-diisopropylbenzene was used as an internal standard substance.

Examples 47 and 48

Electrolytic reductions were carried out in the same manner as in Example 35 except for passing the amounts of electricity shown in Table 7.

TABLE 7

Study of Amounts of Electricity Passed

| | Amount of Electricity Passed (F/mol) | Yield (%)[a] | |
|---|---|---|---|
| | | Triphenylphosphine | Raw Material Collection |
| Example 47 | 2 | 72 | 15 |
| Example 48 | 4 | 82 | 7 |

[a]Yields were measured by detection by gas chromatography.

1,4-diisopropylbenzene was used as an internal standard substance.

Examples 49, 50 and 51

Electrolytic reductions were carried out in the same manner as in Example 35 except for using phosphine oxide shown in Table 8 in place of triphenylphosphine oxide.

TABLE 8

Study of Aryl Groups such as Phenyl Group and Heteroaromatic Ring Group Having Substituent

| | | Yield (%)[a] | |
|---|---|---|---|
| | Phosphine Oxide | Phosphine Derivative | Raw Material Collection |
| Example 49 | Tri(o-tolyl)phosphine Oxide | 75 | 12 |
| Example 50 | Trimesitylphosphine Oxide | 73 | 17 |
| Example 51 | Trifurylphosphine Oxide | 70 | 23 |

[a]Yields were measured by detection by gas chromatography.

1,4-diisopropylbenzene was used as an internal standard substance.

INDUSTRIAL APPLICABILITY

The technology of the present invention can be suitably used in the fields of pharmaceutical and chemical industries and the like.

The invention claimed is:

1. A method for producing $Ar_nR_{3-n}P$ from $Ar_nR_{3-n}P{=}O$, comprising:
   (I) mixing the $Ar_nR_{3-n}P{=}O$ with a chlorinating agent in a polar organic solvent, to cause a reaction; and
   (II-1) adding a salt of a metal having an ionization tendency equal to or lower than that of aluminum to the reaction mixture, to carry out a reduction reaction in the presence of aluminum, or (II-2) subjecting the reaction mixture to electrolytic reduction,
   and thereby producing the $Ar_nR_{3-n}P$;
   wherein Ar represents an aryl group; R represents an aliphatic hydrocarbon group or an aliphatic hydrocarbon group having a substituent; and n represents an integer of 0 to 3.

2. The method according to claim 1, wherein the $Ar_nR_{3-n}P$ is produced by the reduction reaction in (II-1), and when adding the salt of a metal having an ionization tendency equal to or lower than that of aluminum, aluminum is also added to the reaction mixture.

3. The method according to claim 1, wherein the $Ar_nR_{3-n}P$ is produced by the reduction reaction in (II-1), and when mixing the $Ar_nR_{3-n}P{=}O$ with the chlorinating agent in the polar organic solvent, aluminum is also mixed.

4. The method according to claim 1, wherein the chlorinating agent is any one of oxalyl chloride, phosgene, diphosgene, and thionyl chloride.

5. The method according to claim 1, wherein the $Ar_nR_{3-n}P{=}O$ is used in an amount of 5 to 50% by mass of the polar organic solvent.

6. The method according to claim 1, wherein the $Ar_nR_{3-n}P$ is produced by the reduction reaction in (II-1), and aluminum is used in an amount of 0.66 to 5 mol based on 1 mol of the $Ar_nR_{3-n}P{=}O$.

7. The method according to claim 1, wherein the $Ar_nR_{3-n}P$ is produced by the reduction reaction in (II-1), and the salt of a metal is a salt of a metal having an ionization tendency equal to or lower than that of tin.

8. The method according to claim 1, wherein the $Ar_nR_{3-n}P$ is produced by the reduction reaction in (II-1), and a chloride, a bromide, an iodide, a perchlorate, a sulfate, or a nitrate of a metal from groups 4 to 15 of the periodic table is used as the salt of a metal having an ionization tendency equal to or lower than that of aluminum.

9. The method according to claim 1, wherein the $Ar_nR_{3-n}P$ is produced by the reduction reaction in (II-1), and the salt of a metal is a chloride or bromide of a metal having an ionization tendency equal to or lower than that of tin.

10. The method according to claim 1, wherein the $Ar_nR_{3-n}P$ is produced by the reduction reaction in (II-1), and the salt of a metal having an ionization tendency equal to or lower than that of aluminum is used in an amount of 0.0001 to 1 mol based on 1 mol of aluminum.

11. The method according to claim 1, wherein the polar organic solvent is an aprotic polar organic solvent.

12. The method according to claim 1, wherein the polar organic solvent is acetonitrile or a mixed solvent comprising acetonitrile as a main solvent.

13. The method according to claim 1, wherein the $Ar_nR_{3-n}P$ is produced by the reduction reaction in (II-1), and at that time, the reduction reaction is carried out in the presence of excess aluminum, and the $Ar_nR_{3-n}P{=}O$, the chlorinating agent, and the polar organic solvent are further added to the aluminum collected after the reduction reaction, to produce the $Ar_nR_{3-n}P$.

14. A method for producing $Ar_3P$, comprising subjecting a mixture of $Ar_3P{=}O$ with a chlorinating agent to electrolytic reduction in a polar organic solvent;
   wherein, Ar represents an aryl group.

15. A method for producing $Ar_3P$ from $Ar_3P{=}O$, comprising:
   mixing the $Ar_3P{=}O$ with a chlorinating agent in a polar organic solvent, to cause a reaction; and
   adding a salt of a metal having an ionization tendency equal to or lower than that of aluminum to the reaction mixture to carry out a reduction reaction, thereby producing the $Ar_3P$,
   wherein the reduction reaction is carried out in the presence of aluminum;
   and wherein Ar represents an aryl group.

16. The method according to claim 1, wherein Ar is chosen from a phenyl group, a phenyl group having a substituent, a heteroaromatic ring group, and a heteroaromatic ring group having a substituent.

17. The method according to claim 14, wherein Ar is chosen from a phenyl group, a phenyl group having a substituent, or a heteroaromatic ring group.

18. The method according to claim 17, wherein Ar is a phenyl group having a substituent chosen from p-methyl and p-methoxy.

19. The method according to claim 17, wherein Ar is a heteroaromatic ring group chosen from a 2-pyridyl group, a 3-pyridyl group, and a 3-thienyl group.

20. The method according to claim 15, wherein Ar is chosen from a phenyl group, a phenyl group having a substituent, a heteroaromatic ring group, and a heteroaromatic ring group having a substituent.

* * * * *